(12) United States Patent
Li et al.

(10) Patent No.: US 8,399,735 B2
(45) Date of Patent: Mar. 19, 2013

(54) HYDROXYSTEROID DEHYDROGENASE GENE FOR ALTERATION OF PLANT PHENOTYPE

(75) Inventors: Fengling Li, Saskatoon (CA); Adrian Cutler, Saskatoon (CA)

(73) Assignee: National Research Council of Canada, Ottawa, Ontario ( * ) Notice: Subject to any disclaimer, the term of this patent is extended or adjusted under 35 U.S.C. 154(b) by 611 days.

(21) Appl. No.: 12/095,538

(22) PCT Filed: Dec. 1, 2006

(86) PCT No.: PCT/CA2006/001954
§ 371 (c)(1),
(2), (4) Date: Mar. 24, 2010

(87) PCT Pub. No.: WO2007/062522
PCT Pub. Date: Jun. 7, 2007

(65) Prior Publication Data
US 2010/0313295 A1    Dec. 9, 2010

Related U.S. Application Data

(60) Provisional application No. 60/741,065, filed on Dec. 1, 2005.

(51) Int. Cl.
*A01H 1/00* (2006.01)
*A01H 5/00* (2006.01)
*C12N 5/04* (2006.01)
*C12N 5/10* (2006.01)

(52) U.S. Cl. ........ 800/278; 800/281; 800/290; 435/410; 435/419

(58) Field of Classification Search ............... None
See application file for complete search history.

(56) References Cited

U.S. PATENT DOCUMENTS

| | | |
|---|---|---|
| 2002/0040490 A1 | 4/2002 | Gorlach |
| 2004/0010815 A1 | 1/2004 | Lange |
| 2006/0150283 A1 * | 7/2006 | Alexandrov et al. ......... 800/288 |

FOREIGN PATENT DOCUMENTS

| | | |
|---|---|---|
| WO | WO02/10210 | 2/2002 |
| WO | WO 02/10210 | * 2/2002 |

OTHER PUBLICATIONS

WO 02/10210, Feb. 2002, selected pages.*
Lin and Tzen, Plant Physiology and Biochemistry, 2004, vol. 42, pp. 601-608.*
Li Fengling et al: "Transcriptional profiling of imbibed *Brassica napus* seed" Genomics, vol. 86, No. 6, Aug. 26, 2005, pp. 718-730, XP002511003 ISSN: 0888-7643.
Sato S et al: "Structural Analysis of *Arabudopsis thaliana* Chromosome 5. X. Sequence Features of the REgions of 3,076,755 BP Covered by Sixty P1 and TAC Clones" DNA Research, Universal Academy Press, JP, vol. 7, Feb. 1, 2000, pp. 31-63, XP000946868 ISSN: 1340-2838.
Asami Tadao et al: "A mammalian steroid action inhibitor spironolactone retards plant growth by inhibition of brassinosteroid action and induces light-induced gene expression in the dark" Journal of Steroid Biochemistry and Molecular Biology, vol. 91, No. 1-2, Jun. 2004, pp. 41-47, XP002511004.
Li Fengling et al: "A putative hydroxysteroid dehydrogenase involved in regulating plant growth and develpment" Plant Physiology (Rockville), vol. 145, No. 1, Sep. 2007, pp. 87-97, XP002511005 ISSN: 0032-0889.
Shimada K et al: "Gas chromatography and high-performance liquid chromatography of natural steroids" Journal of Chromotagraphy, Elsevier Science Publishers B.V. Amsterdam, NL, vol. 935, No. 1-2, Nov. 23, 2001, pp. 141-172, XP004322069 ISSN: 0021-9673.
Nakamuray *Arabidopsis thaliana* genomic DNA, chromosome 5, P1 clone:MBA10 Genbank Database [online] NCBI, Bethesda MD, USA Accession AB025619, Feb. 14, 2004.

* cited by examiner

*Primary Examiner* — Eileen B O Hara
(74) *Attorney, Agent, or Firm* — Michael R. Williams; Ade & Company Inc.

(57) ABSTRACT

The present invention describes a novel plant hydroxysteroid dehydrogenase gene, (HSD) that is involved in a variety of physiological processes in higher plants. The novel gene product has a degree of similarity to mammalian β-11-hydroxysteroid dehydrogenase genes, known to control the conversion of steroids from active to inactive forms. In plants, the over expression of the HSD gene results in transgenic plants with significantly greater biomass and vigor, increased seed yield, increased tolerance to salt and a suppression of ABA mediated seed dormancy.

6 Claims, 7 Drawing Sheets

A

```
  1 MELINDFLNL TAPFFTFFGL CFFLPPFYFF KFLQSIFSTI FSENLYGKVV
 51 LITGASSGIG EQLAYEYACR GACLALTARR KNRLEEVAEI ARELGSPNVV
101 TVHADVSKPD DCRRIVDDTI THFGRLDHLV NNAGMTQISM FENIEDITRT
151 KAVLDTNFWG SVYTTRAALP YLRQSNGKIV AMSSSAAWLT APRMSFYNAS
201 KAALLSFFET MRIELGGDVH ITIVTPGYIE SELTQGKYFS GEGELIVNQD
251 MRDVQVGPFP VASASGCAKS IVNGVCRKQR YVTEPSWFKV TYLWKVLCPE
301 LIEWGCRLLY MTGTGMSEDT ALNKRIMDIP GVRSTLYPES IRTPEIKSD
```

B

```
At-HSD1    1 -------------------MELINDFLNLTAPFFTFFGL---------CFFLPPFYFFKF
Hs-HSD     1 MERWPWPSGGAWLLVAARALLQLLRSDLRLGRPLLAALALLAALDWLCQRLLPPPAALAV
Mm-HSD     1 -----------------------------MAVM--------KNMLLPILVLSL

At-HSD1   33 LQS--IFST----IFSENL--YGKVVLITGASSGIGEQLAYEYACRGACLALTARRKNRLE
Hs-HSD    61 LAAAGWIALSRLARPQRLPVATRAVLITGCDSGFGKETAKKLDSMGFTVFATV-----LE
Mm-HSD    17 AYY--YMSTNEEFRPEML--QGKKVIVTGASKGIGREMAYHLSKMGAHVMLTARSEEGLQ

At-HSD1   86 EVAEIARELG---SPNVVTVHADVSKPDDCRRIVDDTITHFGRLDHL-V-NNAGMTQISM
Hs-HSD   116 LNSPGAIELRTCCSPRLRLLQMDLTKPGDISRVLEFTKAHTTSTGLWGLVNNAGHNEVVA
Mm-HSD    73 KVVSRCIELG---AASAHYIAGTMEDMTFAEQFTVKAGKLMGGLDMI-IENHITQTSLSL

At-HSD1  141 FENIEDITRTKAVLDTNFWGSVYTTRAALPYLRQSNGKIVANSSSAAWLTAPRMSFYNAS
Hs-HSD   176 DAFLSPVATFFRSCMEVNFFGALELTKGLLPLLRSSRGRIVTVGSPAGDVPYPCLGAYGTS
Mm-HSD   129 FHD--DIHSVRRVMEVNFLSYVVMSTAALPVLKQSNGSIAVLSSLAGKMTQPMIAPYSAS

At-HSD1  201 KAALLSFFETMRIEL----GGDVHITIVTPGYIESELTQ--------------
Hs-HSD   236 KAAVALLMDTFSCELLPWG--VKVSTIIQPGCFKTESVRNVGQWEKRKQLLLANLPQELLQ
Mm-HSD   187 KFALDGFFSTERTELYITKVNVSITLCVLGLIFTE-TA--------------
```

WT　　　　　　　　　　　AOHSD　　　　　NaCl (mM)

B.

SEQUENCE LISTING

```
<160> NUMBER OF SEQ ID NOS: 8

<210> SEQ ID NO 1
<211> LENGTH: 1986
<212> TYPE: DNA
<213> ORGANISM: Arabidopsis thaliana

<400> SEQUENCE: 1
gagagctaaa tcatttacgt tttgatcgac aaaaatggag ttgataaacg actttctcaa      60
cctaactgct cctttcttca ccttctttgg tctctgcttc ttcttgcctc cttttactt     120 cttcaagttc ttgcagtcta ttttctcgac aattttctct gaaaatcttt acgggaaagt    180
tgttctcatc actggtgctt cctccggtat aggcgaggtt tggtcataat gcctttattt    240
taaaattgta gacttaataa cctaattggt cactggtaca atagtactaa gtttcacaca    300
tttaatctta aatgattaat ttatatcatc atgactttca gtgctacaat tatcagtgta    360
ttttcagggt aaaacattag gttttttttct aacaaatata tatatgaata agaaaatata    420
aatgataaaa caaaaaaaaa caaaaaacat ataaacgata tttttgtgaa acggatatat    480
attttatatg gtaaaatgat tgatttgagt ctatttgcgt atatgaaata tcagcaattg    540
gcatatgagt acgcatgtag aggtgcatgt ttagccctga ccgcccgaag gaagaaccgt    600
ctagaggaag tggcagagat tgctcgtgaa ctcggatctc ccaatgttgt taccgttcat    660
gctgatgtct ccaaacctga tgactgtaga cgaatcgttg atgacaccat cacccatttt    720
ggcagatgta agtcacgcca cgggacgcta atcactatca ctctatcaaa accgaccgtt    780
tttttgttac cattcacaag tttggtctac aaaacattga atttctttgg tcttgcagtg    840
gatcatcttg taaataatgc tgggatgacg cagatttcaa tgtttgagaa cattgaagat    900
ataacgagga caaaagcagt tttggtaatt aaaataatta attaccaacc ctttaatttt    960
attcgttgtc ctgatcttta atgaatgatt tgtgattaat taggatacta acttctgggg   1020
atcggtttat accactcgtg ctgcgcttcc ataccttaga caaagtaatg gtaagattgt   1080
ggctatgtcg tcttccgcag cgtggctaac cgctccaagg atgagttttt acaatgtaag   1140
tatatattca cttctttttaa ttacttagta aagtaagctc ttagggattg atgaatatta   1200
```

-continued

| | |
|---|---|
| ttatacatat aatatgttaa ttaggcaagc aaagcagctt tgttgagctt ctttgagacg | 1260 |
| atgagaattg agcttggtgg cgatgtacac attacaatcg tcacacctgg ttatatcgag | 1320 |
| tcggagctca cacaaggcaa gtacttctct ggtgaaggcg agttaatagt caaccaagac | 1380 |
| atgagagatg taagttaaat aaatctttaa ctccttaacc aatataatta atattgaggt | 1440 |
| cattgttgaa ttgtgtgttc ttttgcccaa aattaactag gttcaagtag gaccatttcc | 1500 |
| ggtagcgtca gcatcaggat gtgccaagtc gatagtgaac ggtgtgtgcc ggaaacaaag | 1560 |
| atacgtgaca gagccatcat ggtttaaggt gacgtacctt tggaaagtgc tatgtccgga | 1620 |
| gttgattgag tggggttgtc ggttactgta catgactgga actggtatgt ccgaggatac | 1680 |
| tgcactcaac aagaggatca tggacattcc tggtgtacgt agtactctgt acccggaatc | 1740 |
| tatcagaact ccagaaatca agtcggatta gagaggggtc aatacataat aaatggatga | 1800 |
| gatgtatcat gagtatgtgc aatgagtaat aattatcaaa gaaatgggtg aaaatgtagg | 1860 |
| tttgttttg ttaatggtac ttttgactat gtatattaac tatgtgtctt aagaataag | 1920 |
| tgagttgcct aatactaaac atgtgtgtat cgaaacagaa gagaatccaa ccatactgaa | 1980 |
| atattt | 1986 |

<210> SEQ ID NO 2
<211> LENGTH: 1173
<212> TYPE: DNA
<213> ORGANISM: Arabidopsis thaliana

<400> SEQUENCE: 2

| | |
|---|---|
| atttacgttt tgatcgacaa aaatggagtt gataaacgac tttctcaacc taactgctcc | 60 |
| tttcttcacc ttctttggtc tctgcttctt cttgcctcct ttttacttct tcaagttctt | 120 |
| gcagtctatt ttctcgacaa ttttctctga aaatctttac gggaaagttg ttctcatcac | 180 |
| tggtgcttcc tccggtatag cgagcaatt ggcatatgag tacgcatgta gaggtgcatg | 240 |
| tttagccctg accgccgaa ggaagaaccg tctagaggaa gtggcagaga ttgctcgtga | 300 |
| actcggatct cccaatgttg ttaccgttca tgctgatgtc tccaaacctg atgactgtag | 360 |
| acgaatcgtt gatgacacca tcacccattt tggcagattg gatcatcttg taaataatgc | 420 |
| tgggatgacg cagatttcaa tgtttgagaa cattgaagat ataacgagga caaaagcagt | 480 |
| tttggatact aacttctggg gatcggttta taccactcgt gctgcgcttc catacctag | 540 |
| acaaagtaat ggtaagattg tggctatgtc gtcttccgca gcgtggctaa ccgctccaag | 600 |
| gatgagtttt tacaatgcaa gcaaagcagc tttgttgagc ttctttgaga cgatgagaat | 660 |
| tgagcttggt ggcgatgtac acattacaat cgtcacacct ggttatatcg agtcggagct | 720 |
| cacacaaggc aagtacttct ctggtgaagg cgagttaata gtcaaccaag acatgagaga | 780 |
| tgttcaagta ggaccatttc cggtagcgtc agcatcagga tgtgccaagt cgatagtgaa | 840 |
| cggtgtgtgc cggaaacaaa gatacgtgac agagccatca tggtttaagg tgacgtacct | 900 |
| ttggaaagtg ctatgtccgg agttgattga gtggggttgt cggttactgt acatgactgg | 960 |
| aactggtatg tccgaggata ctgcactcaa caagaggatc atggacattc ctggtgtacg | 1020 |
| tagtactctg tacccggaat ctatcagaac tccagaaatc aagtcggatt agagaggggt | 1080 |
| caatacataa taaatggatg agatgtatca tgagtatgtg caatgagtaa taattatcaa | 1140 |
| agaaatgggt gaaaatgtag gtttgttttt gtt | 1173 |

<210> SEQ ID NO 3
<211> LENGTH: 1299

```
<212> TYPE: DNA
<213> ORGANISM: Arabidopsis thaliana

<400> SEQUENCE: 3
gagagctaaa tcatttacgt tttgatcgac aaaaatggag ttgataaacg actttctcaa      60
cctaactgct cctttcttca ccttctttgg tctctgcttc ttcttgcctc cttttactt     120 cttcaagttc ttgcagtcta tttctcgac aattttctct gaaatctttt acgggaaagt     180
tgttctcatc actggtgctt cctccggtat aggcgagcaa ttggcatatg agtacgcatg     240
tagaggtgca tgtttagccc tgaccgcccg aaggaagaac cgtctagagg aagtggcaga     300
gattgctcgt gaactcggat ctcccaatgt tgttaccgtt catgctgatg tctccaaacc     360
tgatgactgt agacgaatcg ttgatgcac catcacccat tttggcagat tggatcatct     420
tgtaaataat gctgggatga cgcagatttc aatgtttgag aacattgaag atataacgag     480
gacaaaagca gttttggata ctaacttctg gggatcggtt tataccactc gtgctgcgct     540 tccataccttt agacaaagta atggtaagat tgtggctatg tcgtcttccg cagcgtggct     600
aaccgctcca aggatgagtt tttacaatgc aagcaaagca gctttgttga gcttctttga     660
gacgatgaga attgagcttg gtggcgatgt acacattaca atcgtcacac ctggttatat     720
cgagtcggag ctcacacaag gcaagtactt ctctggtgaa ggcgagttaa tagtcaacca     780
agacatgaga gatgttcaag taggaccatt tccggtagcg tcagcatcag gatgtgccaa     840
gtcgatagtg aacggtgtgt gccggaaaca agatacgtg acagagccat catggtttaa     900
ggtgacgtac ctttggaaag tgctatgtcc ggagttgatt gagtgggtt gtcggttact     960 gtacatgact ggaactggta tgtccgagga tactgcactc aacaagagga tcatggacat    1020
tcctggtgta cgtagtactc tgtacccgga atctatcaga actccagaaa tcaagtcgga    1080
ttagagaggg gtcaatacat aataaatgga tgagatgtat catgagtatg tgcaatgagt    1140
aataattatc aaagaaatgg gtgaaaatgt aggttttgttt ttgttaatgg tacttttgac    1200
tatgtatatt aactatgtgt ctttaagaat aagtgagttg cctaatacta aacatgtgtg    1260
tatcgaaaca gaagagaatc caaccatact gaaatattt                            1299

<210> SEQ ID NO 4
<211> LENGTH: 53
<212> TYPE: DNA
<213> ORGANISM: artificial sequence
<220> FEATURE:
<223> OTHER INFORMATION: primer for pcr amplification (5')

<400> SEQUENCE: 4
ggggacaagt ttgtacaaaa aagcaggcta tggagttgat aaacgacttt ctc            53

<210> SEQ ID NO 5
<211> LENGTH: 53
<212> TYPE: DNA
<213> ORGANISM: artificial sequence
<220> FEATURE:
<223> OTHER INFORMATION: amplification primer (3')

<400> SEQUENCE: 5
ggggaccact ttgtacaaga aagctgggtc taatccgact tgatttctgg agt            53

<210> SEQ ID NO 6
<211> LENGTH: 349
<212> TYPE: PRT
<213> ORGANISM: Arabidopsis thaliana

<400> SEQUENCE: 6
```

```
Met Glu Leu Ile Asn Asp Phe Leu Asn Leu Thr Ala Pro Phe Phe Thr
1               5                   10                  15

Phe Phe Gly Leu Cys Phe Phe Leu Pro Pro Tyr Phe Phe Lys Phe
            20                  25                  30

Leu Gln Ser Ile Phe Ser Thr Ile Phe Ser Glu Asn Leu Tyr Gly Lys
        35                  40                  45

Val Val Leu Ile Thr Gly Ala Ser Ser Gly Ile Gly Glu Gln Leu Ala
50                  55                  60

Tyr Glu Tyr Ala Cys Arg Gly Ala Cys Leu Ala Leu Thr Ala Arg Arg
65                  70                  75                  80

Lys Asn Arg Leu Glu Glu Val Ala Glu Ile Ala Arg Glu Leu Gly Ser
                85                  90                  95

Pro Asn Val Val Thr Val His Ala Asp Val Ser Lys Pro Asp Asp Cys
            100                 105                 110

Arg Arg Ile Val Asp Asp Thr Ile Thr His Phe Gly Arg Leu Asp His
            115                 120                 125

Leu Val Asn Asn Ala Gly Met Thr Gln Ile Ser Met Phe Glu Asn Ile
130                 135                 140

Glu Asp Ile Thr Arg Thr Lys Ala Val Leu Asp Thr Asn Phe Trp Gly
145                 150                 155                 160

Ser Val Tyr Thr Thr Arg Ala Ala Leu Pro Tyr Leu Arg Gln Ser Asn
                165                 170                 175

Gly Lys Ile Val Ala Met Ser Ser Ala Ala Trp Leu Thr Ala Pro
            180                 185                 190

Arg Met Ser Phe Tyr Asn Ala Ser Lys Ala Ala Leu Leu Ser Phe Phe
            195                 200                 205

Glu Thr Met Arg Ile Glu Leu Gly Gly Asp Val His Ile Thr Ile Val
210                 215                 220

Thr Pro Gly Tyr Ile Glu Ser Glu Leu Thr Gln Gly Lys Tyr Phe Ser
225                 230                 235                 240

Gly Glu Gly Glu Leu Ile Val Asn Gln Asp Met Arg Asp Val Gln Val
                245                 250                 255

Gly Pro Phe Pro Val Ala Ser Ala Ser Gly Cys Ala Lys Ser Ile Val
            260                 265                 270

Asn Gly Val Cys Arg Lys Gln Arg Tyr Val Thr Glu Pro Ser Trp Phe
            275                 280                 285

Lys Val Thr Tyr Leu Trp Lys Val Leu Cys Pro Glu Leu Ile Glu Trp
            290                 295                 300

Gly Cys Arg Leu Leu Tyr Met Thr Gly Thr Gly Met Ser Glu Asp Thr
305                 310                 315                 320

Ala Leu Asn Lys Arg Ile Met Asp Ile Pro Gly Val Arg Ser Thr Leu
                325                 330                 335

Tyr Pro Glu Ser Ile Arg Thr Pro Glu Ile Lys Ser Asp
            340                 345

<210> SEQ ID NO 7
<211> LENGTH: 295
<212> TYPE: PRT
<213> ORGANISM: Homo sapiens

<400> SEQUENCE: 7

Met Glu Arg Trp Pro Trp Pro Ser Gly Gly Ala Trp Leu Leu Val Ala
1               5                   10                  15

Ala Arg Ala Leu Leu Gln Leu Leu Arg Ser Asp Leu Arg Leu Gly Arg
            20                  25                  30
```

```
Pro Leu Leu Ala Ala Leu Leu Ala Leu Ala Leu Asp Trp Leu
        35                  40                  45

Cys Gln Arg Leu Leu Pro Pro Ala Ala Leu Ala Val Leu Ala Ala
 50                  55                  60

Ala Gly Trp Ile Ala Leu Ser Arg Leu Ala Arg Pro Gln Arg Leu Pro
 65                  70                  75                  80

Val Ala Thr Arg Ala Val Leu Ile Thr Gly Cys Asp Ser Gly Phe Gly
                 85                  90                  95

Lys Glu Thr Ala Lys Lys Leu Asp Ser Met Gly Phe Thr Val Asp Ala
                100                 105                 110

Thr Val Leu Glu Leu Asn Ser Pro Gly Ala Ile Glu Leu Arg Thr Cys
            115                 120                 125

Cys Ser Pro Arg Leu Arg Leu Leu Gln Met Asp Leu Thr Lys Pro Gly
130                 135                 140

Asp Ile Ser Arg Val Leu Glu Phe Thr Lys Ala His Thr Thr Ser Thr
145                 150                 155                 160

Gly Leu Trp Gly Leu Val Asn Asn Ala Gly His Asn Glu Val Val Ala
                165                 170                 175

Asp Ala Glu Leu Ser Pro Val Ala Thr Phe Arg Ser Cys Met Glu Val
                180                 185                 190

Asn Phe Phe Gly Ala Leu Glu Leu Thr Lys Gly Leu Leu Pro Leu Leu
                195                 200                 205

Arg Arg Ser Ser Arg Gly Arg Ile Val Thr Val Gly Ser Pro Ala Gly
    210                 215                 220

Asp Met Pro Tyr Pro Cys Leu Gly Ala Tyr Gly Thr Ser Lys Ala Ala
225                 230                 235                 240

Val Ala Leu Leu Met Asp Thr Phe Ser Cys Glu Leu Leu Pro Trp Gly
                245                 250                 255

Val Lys Val Ser Ile Ile Gln Pro Gly Cys Phe Lys Thr Glu Ser Val
                260                 265                 270

Arg Asn Val Gly Gln Trp Glu Lys Arg Lys Gln Leu Leu Leu Ala Asn
            275                 280                 285

Leu Pro Gln Glu Leu Leu Gln
        290                 295

<210> SEQ ID NO 8
<211> LENGTH: 223
<212> TYPE: PRT
<213> ORGANISM: Mus musculus

<400> SEQUENCE: 8

Met Ala Val Met Lys Asn Tyr Leu Leu Pro Ile Leu Val Leu Ser Leu
 1               5                  10                  15

Ala Tyr Tyr Tyr Tyr Ser Thr Asn Glu Glu Phe Arg Pro Glu Met Leu
                20                  25                  30

Gln Gly Lys Lys Val Ile Val Thr Gly Ala Ser Lys Gly Ile Gly Arg
            35                  40                  45

Glu Met Ala Tyr His Leu Ser Lys Met Gly Ala His Val Val Leu Thr
        50                  55                  60

Ala Arg Ser Glu Glu Gly Leu Cys Lys Val Val Ser Arg Cys Leu Glu
 65                  70                  75                  80

Leu Gly Ala Ala Ser Ala His Tyr Ile Ala Gly Thr Met Glu Asp Met
                 85                  90                  95

Thr Phe Ala Glu Gln Phe Ile Val Lys Ala Gly Lys Leu Met Gly Gly
                100                 105                 110
```

-continued

```
Leu Asp Met Leu Ile Leu Asn His Ile Thr Gln Thr Ser Leu Ser Leu
        115                 120                 125

Phe His Asp Asp Ile His Ser Val Arg Arg Val Met Glu Val Asn Phe
        130                 135                 140

Leu Ser Tyr Val Val Met Ser Thr Ala Ala Leu Pro Met Leu Lys Gln
145                 150                 155                 160

Ser Asn Gly Ser Ile Ala Val Ile Ser Ser Leu Ala Gly Lys Met Thr
                165                 170                 175

Gln Pro Met Ile Ala Pro Tyr Ser Ala Ser Lys Phe Ala Leu Asp Gly
            180                 185                 190

Phe Phe Ser Thr Met Arg Thr Glu Leu Tyr Ile Thr Lys Val Asn Val
        195                 200                 205

Ser Ile Thr Leu Cys Val Leu Gly Leu Ile Asp Thr Glu Thr Ala
        210                 215                 220
```

HYDROXYSTEROID DEHYDROGENASE GENE FOR ALTERATION OF PLANT PHENOTYPE

PRIOR APPLICATION INFORMATION

This application claims the benefit of U.S. Provisional Application 60/741,065, filed Dec. 1, 2005.

FIELD OF THE INVENTION

The present invention relates to the field of plant biotechnology and specifically to methods of enhancing the performance of plants by expression of a steroid dehydrogenase gene. Expression of this gene, believed to be involved in the mechanism of brassinosteroid formation and/or action, results in plants demonstrating increased vigour and photosynthetic capacity resulting in larger plants with increased vegetative and seed yield. Expression of the HSD gene additionally increases the ability of plants to tolerate salt stress and results in the formation of seeds not subject to ABA mediated dormancy.

BACKGROUND OF THE INVENTION

1. Technical Field

Brassinosteroids are a class of plant growth regulatory substances found in low concentrations in all species of plants that have been examined. Brassinolide, one of the major types of the 40 or so brassinosteroids that have been described, was first discovered in the pollen of *Brassica napus*, (rapeseed), Grove et al., Nature 281:216, 1979.

Brassinosteroids produce a variety of useful phenotypic changes in plants that include: acceleration of seed germination and increased vigour of seedlings, increased cell size and elongation resulting in larger plants with increased biomass and seed yield, increased photosynthetic capacity and resistance to fungal and bacterial pathogens, Mandava et al., An. Rev. Plant Physiol. Plant Mol. Biol. 39:23, 1988.

The biosynthesis of sterols in plants begins with acetyl CoA and through sequential condensation reactions of the well characterized isoprenoid pathway leads to the formation of squalene, the immediate precursor of sterols in plants.

Further specific aspects of the biosynthesis of brassinosteroids have been discovered using cultured cells and brassinosteroid deficient mutations of *Catharanthus*, (Clouse et al., 1998; Fujoika et al., 2000). Plants with such mutations show a dwarf phenotype that may be rescued by the application of brassinosteroids demonstrating the involvement in one of the biosynthetic steps. Enzymes that are involved in the biosynthetic pathway include sterol desaturases (DWF7/STE1) (Choe et al., 1999b), oxidases (DWF1/DIM1/LKB) (Choe et al., 1999a; Nomura et al., 1999), reductases (DET2/LK) (Li et al., 1996), and cytochrome P450 hydroxylases (DWF4, CPD/DWF3, D) (Choe et al., 1998; Bishop et al., 1999). The known biochemical pathways resulting in the formation of brassinolide are reviewed in Noguchi et al., 2000.

In addition to enzymes involved in biosynthesis additional mutations in *Arabidopsis* and pea have revealed blockages in either brassinosteroid perception or transduction of brassinosteroid mediated responses. The BRI1 protein is a leucine-rich repeat serine/threonine kinase comprising a transmembrane spanning region and an external brassinosteroid binding domain believed to be a receptor protein required for brassinosteroid signal transduction across the plasma membrane. (Li and Chory, 1997; Wang, et al., 2001).

It is clear that brassinosteroids represent an important group of plant growth regulatory substances that affect many aspects of plant metabolism and growth and that modulation of the response to these substances can effect changes in plant development and performance of significant agronomic importance including seedling vigour, seed and biomass yield, tolerance to salt, heat, drought and disease and seed dormancy.

2. State of the Art

Brassinosteroids

Naturally occurring brassinosteroids are only found in minute concentrations in plants thus isolation and use of such compounds for application to plants to effect increases in growth and development are impractical because of the very high costs of extraction. Thompson et al., U.S. Pat. No. 4,346,226 describe the chemical synthesis of synthetic polyhydroxylated steroidal lactones that can be used as synthetic analogues of naturally occurring brassinolides.

Brassinosteroids are produced naturally as the result of a complex multi-step biosynthetic pathway. A number of transgenic approaches to manipulate one or more of the metabolic steps of brassinolide synthesis, degradation or perception have been described. Neff and Chory, U.S. Pat. No. 6,534,313 describe a gene, bas 1 and encoded protein BAS-1 that is a member of the cytochrome P450 family that appears to be a C-26 hydroxylase of brassinolide. Transgenic plants overexpressing the bas 1 gene are dwarfed and show depressed levels of brassinolide and some brassinosteroid precursors suggesting the role of this enzyme is inactivation of the growth promoting effects of brassinolide.

Koncz et al., U.S. Pat. No. 5,952,545 describe an additional P450 cytochrome hydrolylase gene and encoded protein involved in the early steps of brassinolide biosynthesis specifically in the conversion of cathasterone to teasterone. Plants with a mutated gene or a gene with reduced expression show a dwarf phenotype that is restored to wild type by brassinolide. Over expression of this gene however, does not produce plants with an increased growth or development phenotype seen with application of exogenous brassinolide.

Kang and Park, U.S. Pat. No. 6,605,469 describe a dark-inducible cytochrome P450 C-2 hydroxylase involved in the brassinosteroid biosynthetic pathway specifically through conversion of typhasterol to castasterone and 6-deoxotyphasterol to 6-deoxocasterone. The gene, designated ddwf1 and the encoded DDWF1 protein appear to be exclusively involved in the light/dark regulated development of hypocotyls. The DDWF1 protein was shown to interact with Pra-2 a small molecular weight GTP binding protein with known involvement in transduction of dark induced hypocotyl elongation. Transgenic plants overexpressing DDWF1 show increased elongation of hypocotyls in both light and dark, however other plants parts are not affected.

Chory and Wang, U.S. Pat. No. 6,768,043 describe an additional P450 cytochrome protein gene DAS5 involved in the biosynthesis of brassinosteroids. When the DAS5 gene is overexpressed in plants, higher levels of several brassinolide precursor molecules are recorded and transgenic plants exhibit an increased growth of up to 26% in fresh weight. The results achieved are consistent with an involvement of the DAS5 gene in the brassinosteroid pathway close to the formation of the active growth regulator brassinolide. Physiological effects of the overexpression of DAS5 in addition to increased growth were not reported.

Chory and Li, U.S. Pat. No. 6,245,969; U.S. Pat. No. 6,765,085 describe a trans-membrane receptor kinase gene, BIN 1 and transcribed polypeptide, comprising a brassinosteroid receptor. The BIN1 polypeptide has an extracellular brassinosteroid binding domain of 70 amino acids that functions as an extracellular domain receptor. The 70 amino acid island region is required for brassinosteroid binding whereas the trans-membrane receptor kinase activity transduces steroid signals across the plasma membrane. Overexpression of BIN1 in transgenic plants is suggested to result in plants characterized as having increased plant yield or vegetative biomass, however, examples of such effects are not provided.

Finally, Chory and Wang, U.S. Pat. No. 6,921,848, describe the BZR1 gene, and an altered bzr-1D gene involved in the brassinosteroid response pathway. The BZR1 protein and the bzr1-D protein appear to act downstream of the brassinosteroid receptor BIN 1. Expression of BZR1 genes in transgenic plants is proposed to cause such plants to grow larger and have increased yield in comparison with wild type plants however, examples of such effects are not provided.

SUMMARY OF THE INVENTION

The present invention describes the discovery, characterization and use of a novel β-11-hydroxysteroid dehydrogenase gene of plant origin.

More specifically, the present invention relates to an isolated polynucleotide sequence comprising a nucleotide sequence as identified in Seq. I.D. No. 1, encoding a polypeptide as identified in Seq. I.D. No. 6. The protein sequence has 43% sequence identity and 60% sequence similarity over 150 amino-acids, based on Clustal W vers. 1.8, to mammalian β-11-hydroxysteroid dehydrogenase polypeptides.

The present invention also relates to an isolated polynucleotide comprising the complement (antisense) of said isolated polynucleotide sequences.

Additionally, the present invention relates to a chimeric gene comprising said polynucleotide sequences operably linked to regulatory sequences active in host cells. Said host cells may be a plant, yeast or bacterial cells.

Furthermore said invention relates to a process for producing an isolated plant cell comprising said chimeric gene sequences and regeneration of functional transformed plants expressing said chimeric gene sequences.

An additional embodiment of the present invention provides a method of generating a transformed plant comprising said chimeric gene sequences that has increased seedling vigour, increased mature plant size and increased biomass and seed yield in comparison to equivalent non-transformed plants.

A further embodiment of the present invention provides a method of generating a transformed plant comprising said chimeric gene sequences that has increased stress tolerance and or pathogen resistance in comparison to equivalent non-transformed plants.

A still further embodiment of the present invention is the production of plant seed comprising said chimeric gene sequences that has reduced or significantly altered dormancy characteristics.

According to a first aspect of the invention, there is provided a method for altering expression levels of a hydroxysteroid dehydrogenase protein in a plant by introducing a nucleic acid molecule derived from at least a portion of the nucleic acid sequence as set forth in SEQ ID No. 1, said nucleic acid molecule being arranged for expression in said plant and expression of said nucleic acid molecule leading to altered levels of HSD protein compared to an unmodified control plant.

According to a second aspect of the invention, there is provided a method of expressing an HSD gene in a plant comprising the steps of:

a) Introducing into a plant cell capable of being transformed a genetic construct comprising a first DNA expression cassette that comprises a DNA sequence that encodes a HSD peptide having at least 50% identity to Seq. ID No. 6, operably linked to a suitable transcriptional regulatory region and, b) recovery of a plant which comprises said DNA sequence.

According to a third aspect of the invention, there is provided a method for altering the growth characteristics of a plant comprising:

Introducing into a plant cell capable of being transformed and regenerated to a whole plant, a genetic construct comprising a DNA sequence derived from Seq. ID. No. 1, operably linked to a suitable transcriptional regulatory region and recovering a plant which contains said recombinant DNA.

BRIEF DESCRIPTION OF THE DRAWINGS

FIG. 1A: Shows the amino acid sequence of the *Arabidopsis* AtHSD1 protein. This is already recited as Seq ID No 6

FIG. 1B Shows the amino acid sequence similarity of the Arabidopsis AtHSD1 gene (SEQ ID NO: 6) to human (SEQ ID NO: 7) and mouse (SEQ ID NO: 8) HSD genes.

Figure 2:
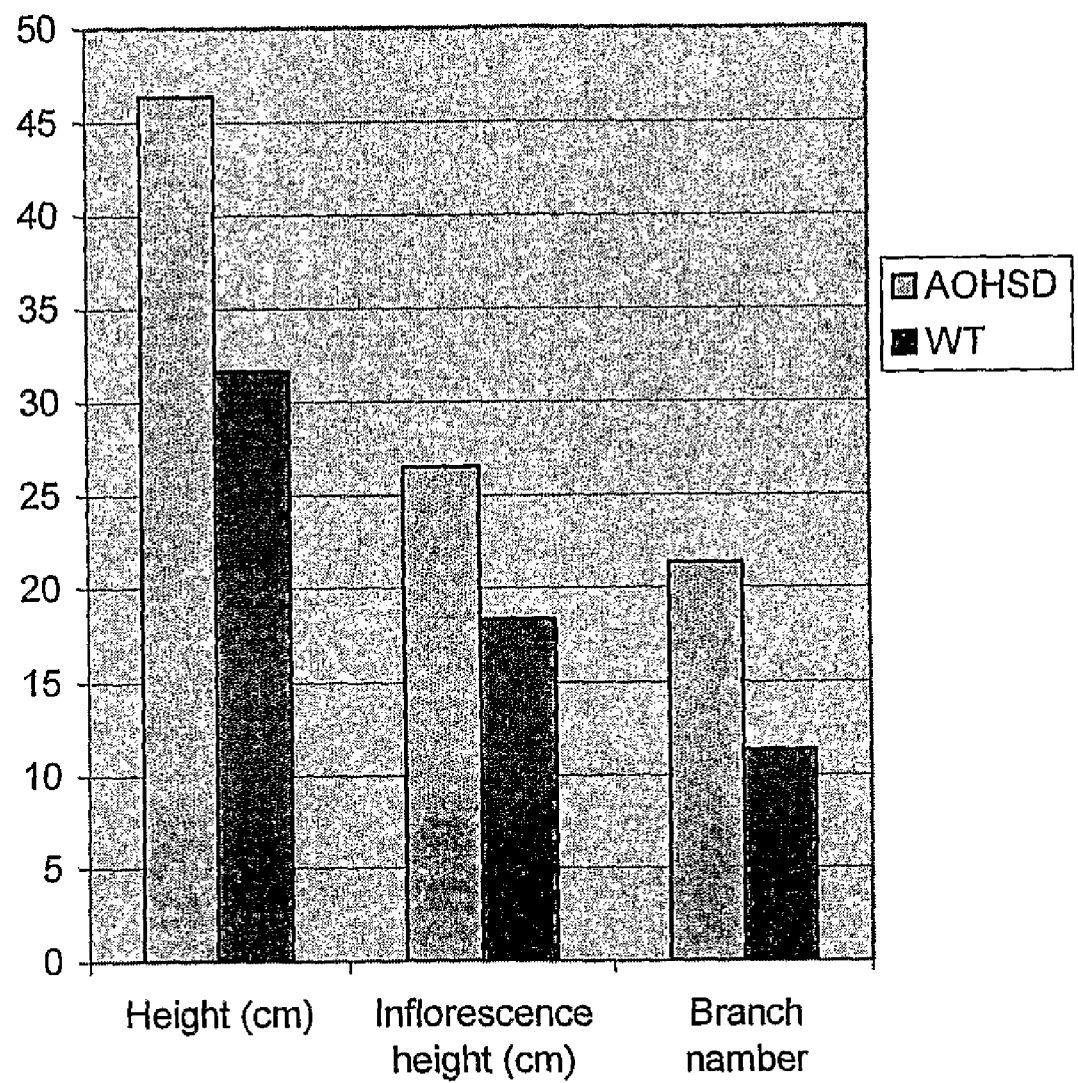
FIG. 2: Shows a comparison of growth and development parameters between transformed (AOHSD) and Wild-type (WT) *Arabidopsis* plants

(B) Plants germinated and grown for 2 weeks on standard MS medium supplemented with 100 mM NaCl.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

In order to provide a clear and consistent understanding of the specification and claims, including the scope to be given certain terms used therein, the following definitions are provided.

The singular forms "a," "an," and "the" include plural reference unless the context clearly dictates otherwise.

A "coding sequence" or "coding region" is the part of a gene that codes for the amino acid sequence of a protein, or for a functional RNA such as a tRNA or rRNA. A coding sequence typically represents the final amino acid sequence of a protein or the final sequence of a structural nucleic acid. Coding sequences may be interrupted in the gene by intervening sequences, typically intervening sequences are not found in the mature coding sequence.

A "polynucleotide encoding an amino acid sequence" refers to a nucleic acid sequence that encodes the genetic code of at least a portion of a mature protein sequence, typically a contiguous string of amino acids typically linked through a peptide bond. An "amino acid sequence" is typically two or more amino acid residues, more typically 10 or more amino acids in a specific defined order.

A "complement" or "complementary sequence" is a sequence of nucleotides which forms a hydrogen-bonded duplex with another sequence of nucleotides according to Watson-Crick base-pairing rules. For example, the complementary base sequence for 5'-AGCT-3' is 3'-TCGA-5'.

"Expression" refers to the transcription of a gene into structural RNA (rRNA, tRNA) or messenger RNA (mRNA) with subsequent translation into a protein in the case of the mRNA.

Polynucleotides are "functionally equivalent" if they perform substantially the same biological function. By substantially the same biological function it is meant that similar protein activities or protein function are encoded by a mRNA polynucleotide, or a structural polynucleotide has a similar structure and biological activity.

Polynucleotides are "heterologous" to one another if they do not naturally occur together in the same arrangement in the same organism. A polynucleotide is heterologous to an organism if it does not naturally occur in its particular form and arrangement in that organism.

Polynucleotides or polypeptides have "homologous" or "identical" sequences if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a portion of the sequence to identify and compare local regions. The comparison portion is generally from about 20 to about 200 contiguous nucleotides or contiguous amino acid residues or more. The "percentage of sequence identity" or "percentage of sequence homology" for polynucleotides and polypeptides, such as 50, 60, 70, 80, 90, 95, 98, 99 or 100 percent sequence identity may be determined by comparing two optimally aligned sequences which may or may not include gaps for optimal alignment over a comparison region, wherein the portion of the polynucleotide or polypeptide sequence in the comparison may include additions or deletions (i.e., gaps) as compared to the reference sequence (which does not comprise additions or deletions) for optimal alignment of the two sequences.

The percentage of homology or similarity or identity is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. Readily available sequence comparison and multiple sequence alignment algorithms are, respectively, the Basic Local Alignment Search Tool (BLAST) (Altschul, S. F. et al., 1990. J. Mol. Biol. 215:403; Altschul, S. F. et al., 1997. Nucleic Acids Res. 25: 3389-3402) and ClustalW programs. Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program.

Sequence identity typically refers to sequences that have identical residues in order, whereas sequence similarity refers to sequences that have similar or functionally related residues in order. For example an identical polynucleotide sequence would have the same nucleotide bases in a specific nucleotide sequence as found in a different polynucleotide sequence. Sequence similarity would include sequences that are similar in character for example purines and pyrimidines arranged in a specific fashion. In the case of amino acid sequences, sequence identity means the same amino acid residues in a specific order, where as sequence similarity would allow for amino acids with similar chemical characteristics (for instance basic amino acids, or hydrophobic amino acids) to reside within a specific order.

The terms "stringent conditions" or "stringent hybridization conditions" includes reference to conditions under which a probe will hybridize to its target sequence, to a detectably greater degree than other sequences (e.g. at least 2-fold over background). Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. Exemplary low stringency conditions include hybridization with a buffer solution of 30% formamide, 1 M NaCl, 1% SDS at 37° C., and a wash in 2×SSC at 50° C. Exemplary high stringency conditions include hybridization in 50% formamide, 1 M NaCl, 1% SDS at 37° C., and a wash in 0.1×SSC at 60° C. Hybridization procedures are well-known in the art and are described in Ausubel et al., (Ausubel F. M., et al., 1994, Current Protocols in Molecular Biology, John Wiley & Sons Inc.).

"Isolated" refers to material that is: (1) substantially or essentially free from components which normally accompany or interact with it as found in its naturally occurring environment; or (2) if in its natural environment, the material has been non-naturally altered to a composition and/or placed at a locus in the cell not native to a material found in that environment. The isolated material optionally comprises material not found with the material in its natural environment. For example, a naturally occurring nucleic acid becomes an isolated nucleic acid if it is altered, or if it is transcribed from DNA which is altered, by non-natural, synthetic methods performed within the cell from which it originates.

Two DNA sequences are "operably linked" if the linkage allows the two sequences to carry out their normal functions relative to each other. For instance, a promoter region would be operably linked to a coding sequence if the promoter were capable of effecting transcription of that coding sequence and said coding sequence encoded a product intended to be expressed in response to the activity of the promoter.

A "polynucleotide" is a sequence of two or more deoxyribonucleotides (in DNA) or ribonucleotides (in RNA).

A "DNA construct" is a nucleic acid molecule that is isolated from a naturally occurring gene or which has been modified to contain segments of nucleic acid which are combined and juxtaposed in a manner which would not normally otherwise exist in nature.

A "polypeptide" is a sequence of two or more amino acids.

A "promoter" or transcriptional regulatory region is a cis-acting DNA sequence, generally located upstream of the initiation site of a gene, to which RNA polymerase may bind and initiate correct transcription.

A "recombinant" polynucleotide, for instance a recombinant DNA molecule, is a novel nucleic acid sequence formed through the ligation of two or more nonhomologous DNA molecules (for example a recombinant plasmid containing one or more inserts of foreign DNA cloned into it).

"Transformation" means the directed modification of the genome of a cell by the external application of recombinant DNA from another cell of different genotype, leading to its uptake and integration into the subject cell's genome.

A "transgenic plant" encompasses all descendants, hybrids, and crosses thereof, whether reproduced sexually or asexually, and which continue to harbour the foreign DNA.

"Vigour" means superior size and speed of growth and rate of development, improved health and performance under stressful conditions.

Unless defined otherwise all technical and scientific terms used herein have the same meaning as commonly understood to one of ordinary skill in the art to which this invention belongs.

DESCRIPTION OF SPECIFIC EMBODIMENTS

The present invention describes the cloning, characterization and expression in transgenic plants of nucleic acids encoding a novel plant hydroxysteroid dehydrogenase (HSD) that has a degree of similarity to mammalian β-11-hydroxysteroid dehydrogenases. Transgenic overexpression of the HSD gene and reduction of expression of the HSD gene via expression of antisense genes provides data consistent with the involvement of the novel HSD gene in brassinolide biosynthesis and/or brassinolide signal transduction.

The HSD gene was identified in a study of gene expression in germinating and non-germinating *Brassica napus* seeds. Gene expression was monitored by using *Arabidopsis* cDNA microarrays and the HSD gene was identified as being expressed in non-germinating seed (Li et al, 2005). The sequence of this gene was known from the *Arabidopsis* genome sequence and the full-length gene was obtained from a public repository of expressed sequence tags (ESTs). The effects of this gene were determined by introducing it into *Arabidopsis* and *Brassica* plants under the control of a constitutive promoter and comparing the phenotype of the transformed plants with the phenotypes of control plants.

*Brassica* and *Arabidopsis* are both members of the Crucifer family and are very similar genetically. There is an average of about 86% homology between corresponding *Brassica* and *Arabidopsis* gene coding sequences. However, in general, plant genes "work" in any plant irrespective of the evolutionary distance between the source plant and the target plant. This is now a well-known principle of genetic modification. The principle extends further—many bacterial genes work in plants and animals and some animal genes work in plants and bacteria.

The present invention describes the discovery that the alteration in the expression levels of said gene, in particular the increase in expression of said gene, or the increased expression of an altered protein form of said gene results in changes in seedling vigour, increased plant vegetative growth, increased seed yield, increased tolerance to abiotic stress such as salt tolerance and reduction in seed dormancy which are useful to derive new plant phenotypes and plants with novel utility. Similarly, inhibition of the HSD gene leads to changes in seedling vigour, decreased plant vegetative growth, decreased seed yield, decreased tolerance to abiotic stress such as salt tolerance and alterations in seed dormancy, which may be useful to derive new plant phenotypes and plants with potential novel utility. The results of altered HSD gene expression are to correspondingly alter brassinosteroid effects. Therefore increased HSD gene expression causes enhanced growth and other effects associated with brassinosteroids, whereas the opposite effects are produced by reduction in HSD gene expression. The HSD peptide may be modified so as to enhance its effectiveness in mediating brassinosteroid effects, for example by increasing its stability or inherent enzyme activity.

Within the scope of the present invention, it is contemplated that the expression of a HSD gene, or portions thereof, can include the overexpression of the native protein, or overexpression of a modified protein, or the expression of the nucleic acid in such a fashion as to lead to the inhibition of the native HSD gene. Techniques well-known in the art for suppression of gene expression can include co-suppression, antisense RNA, RNAi or other methods known to inhibit gene expression. Reduction in HSD gene expression may be useful as part of a mechanism to reduce the viability and fertility of the progeny of elite germplasm in order to prevent the unauthorized proliferation of elite germplasm.

It is also contemplated that tissue specific expression of the HSD gene may be achieved by the use of so-called tissue specific promoters or regulatory elements that preferentially express a HSD gene in one or more specific plant tissues.

Accordingly, it is understood that those skilled in the art will readily appreciate that the use of the HSD polynucleotide sequences and HSD-related sequences described herein can be accomplished in a variety of means that include but are not limited to, expression of native or modified versions of the encoded protein, as well as expression of genetic constructs that inhibit the expression of the wild-type gene. This would permit selective expression of HSD effects. For example, expression in vegetative tissue, but not seeds would allow plants to be produced with larger size and vigour, but that retain seed dormancy so that seeds will germinate in the following growing season.

The present invention demonstrates the utility of said HSD nucleic acid sequences and altered forms of the HSD protein encoded by said nucleic acid sequences in controlling plant development and hence assigns a novel utility for the use of the HSD gene to alter growth and performance of field crops.

The nucleic acid sequences provided in the present invention can be used to alter plant phenotype by heterologous expression of the nucleic acid sequence shown in Seq. ID. Nos. 1 & 2.

The nucleic acid sequence of Seq. ID. No. 1 encodes a HSD protein that has been shown in the present invention to be consistent with involvement in brassinosteroid biosynthesis, brassinosteroid perception (sensitivity) or transduction of brassinosteroid activity in pant tissues.

It is contemplated, within the scope of the present invention, that the polynucleotides described in Seq. ID No. 1 can be used to alter brassinosteroid content and affect various plant characteristics, including seedling vigour, increase plant vegetative growth, increased seed yield, increased tolerance to abiotic stress such as salt tolerance and reduction in seed dormancy using methods familiar to those in the art to introduce and express said polynucleotides in plant cells and whole plants.

In one aspect of the present invention, this gene sequence is used to modify seedling vigour.

In another aspect of the present invention, the nucleic acid sequence described in Seq. ID. No. 1 is used to modify plant vegetative growth, In another aspect of the present invention, the nucleic acid sequence described in Seq. ID. No. 1 is used to increase seed yield.

In still another aspect of the present invention, the nucleic acid sequence described in Seq. ID. No. 1 is used to increase tolerance to abiotic stress such as salt tolerance.

In still another aspect of the present invention, the nucleic acid sequence described in Seq. ID. No. 1 is used to affect changes in seed dormancy. Specifically, reducing HSD levels increases the rate and completion of germination while increasing HSD levels makes germination difficult. In agriculture and horticulture it is almost always valuable to reduce dormancy so that plants can be germinated on demand.

The present invention may be practiced in all plant species, including monocots and dicot species. Monocot species will include for example, maize, wheat, triticale, rye, barley, rice, sorghum and other monocotyledonous plant species of interest. Dicot plant species can include, but are not limited to: soybean, *Brassica*, tobacco, cotton, dicot vegetables such as tomato, lettuce, squash, to name only few as examples where the invention may be practiced.

In one particular aspect of the present invention, the nucleic acid described in Seq. ID No. 1 is used to alter the phenotype of an *Arabidopsis* plant by introduction of said nucleic acid or portion thereof into an *Arabidopsis* plant and recovering a plant wherein the plant comprising said genetic construct exhibits one or more of the following altered characteristics when compared with wild type plants: increased seedling vigour, increased plant vegetative growth, increased seed yield, increased tolerance to abiotic stress such as salt tolerance and reduction in seed dormancy.

In still another aspect of the present invention, the nucleic acid described in Seq. ID No. 1 or a sequence related thereto as described herein is used to alter the phenotype of a *Brassica* plant by introduction of said nucleic acid or portion thereof into an *Brassica napus* plant and recovering a plant wherein the plant comprising said genetic construct exhibits one or more of the following altered characteristics when compared with controls, for example, mock transformed or vector transformed or wild type plants of similar type grown under similar conditions: increased seed yield, increased seed mass, increased seedling vigour, increased plant vegetative growth, increased mature plant size, increased biomass, improved growth in nutrient-poor soil, shorter time to maturity, increased tolerance to abiotic stress (e.g. increased salt tolerance and increased temperature tolerance), increased oil content, altered hormone sensitivity (e.g. decreased sensitivity to ABA and/or brassinosteroids), male sterility, and altered seed dormancy.

In one broad aspect of the invention these nucleic acid sequences may be used for identification of related homologous sequences deposited in public databases through comparative techniques well-known in the art, or as hybridization probes for the identification of related cDNA or genomic sequences from various species, including plant species where the DNA sequence information is not known. In particular, it is contemplated that these sequences, so described, can be used for the isolation of plant genes encoding similar activities.

A person skilled in the art can utilize the sequence information provided within the scope of the present invention, including both the polynucleotide and deduced amino acid sequence of Seq. ID. No. 1 to isolate related genes from various other plant species. The similarity or identity of two polypeptide or polynucleotide sequences is determined by comparing sequences. In the art, this is typically accomplished by alignment of the amino acid or nucleotide sequences and observing the strings of residues that match. The identity or similarity of sequences can be calculated by known means including, but not limited to, those described in Computational Molecular Biology, Lesk A. M., ed., Oxford University Press, New York, 1988, Biocomputing: Informatics and Genome Projects, Smith, D. W., ed., Academic Press, New York, 1993., Computer Analysis of Sequence Data, Part I, Griffin, A. M. and Griffin, H. G., eds., Humana Press, New Jersey, 1994 and other protocols known to those skilled in the art. Moreover, programs to determine relatedness or identity are codified in publicly available programs. One of the most popular programs comprises a suite of BLAST programs, three designed for nucleic acid sequences (BLASTN, BLASTX and TBLASTX), and two designed for protein sequences (BLASTP and TBLASTN) (Coulson, Trends in Biotechnology, 12:76-80, 1994). The BLASTX program is publicly available from NCBI and other sources such as the BLAST Manual, Altschul, S., et al., NCBI NLM NIH Bethesda Md. 20984, provides online help and further literature references for BLAST and related protein analysis methods, and Altschul, S., et al., J. Mol. Biol 215:403-410, 1990.

The isolated polynucleotide can be sequenced and the DNA sequence used to further screen DNA sequence collections to identify related sequences from other species. The DNA sequence collections can comprise EST sequences, genomic sequences or complete cDNA sequences.

In a broad aspect of the present invention, nucleic acids encoding a protein at least 50% homologous to the protein encoded by Seq. ID. No. 1 are isolated and said nucleic acids are used to alter the one or more of the following characteristics in a plant species, when contrasted with wild type plants of the same species: increased seedling vigour, increased plant vegetative growth, increased seed yield, increased tolerance to abiotic stress such as salt tolerance and reduction in seed dormancy, through introduction of said nucleic acid or portion thereof into said plant species and recovering a plant wherein the characteristics of the plant have changed as a result of the introduction of the nucleic acid sequence, or portion thereof into the plant species.

In one particular aspect of the present invention, the nucleic acid described in Seq. ID No. 1 is used to alter the phenotype of a Brassica plant by introduction of said nucleic acid or portion thereof into a Brassica plant and recovering a plant wherein the plant comprising said genetic construct exhibits increased seedling vigour when compared to non-transformed plants.

In another particular aspect of the present invention, the nucleic acid described in Seq. ID No. 1 is used to alter the phenotype of a Brassica plant by introduction of said nucleic acid or portion thereof into a Brassica plant and recovering a plant wherein the plant comprising said genetic construct exhibits increased plant vegetative growth when compared to non-transformed plants. As will be appreciated by one of skill in the art, 'non-transformed plants' refers to 'controls' which may also include plants transformed with a vector sequence which lacks a nucleic acid molecule encoding functional HSD which are grown under similar conditions as the transgenic described above.

In still another particular aspect of the present invention, the nucleic acid described in Seq. ID No. 1 is used to alter the phenotype of a Brassica plant by introduction of said nucleic acid or portion thereof into a Brassica plant and recovering a plant wherein the plant comprising said genetic construct exhibits increased seed yield when compared to non-transformed plants.

In one aspect of the present invention that provides a clear indication of the utility of the present invention, the nucleic acid described in Seq. ID No. 1 is used to alter the phenotype of a Brassica plant by introduction of said nucleic acid or portion thereof into a Brassica plant and recovering a plant wherein the plant comprising said genetic construct exhibits increased tolerance to abiotic stress such as salt tolerance when compared to non-transformed plants. As will be appreciated by one of skill in the art, as used herein, 'salt tolerance' refers to the ability of modified plants to survive and grow in the presence of high concentrations of salt in the soil that would kill unmodified plants.

In one aspect of the present invention that provides a novel phenotype, the nucleic acid described in Seq. ID No. 1 is used to alter the phenotype of a Brassica plant by introduction of said nucleic acid or portion thereof into a Brassica plant and recovering a plant wherein the plant comprising said genetic construct exhibits altered seed dormancy when compared to non-transformed plants. For example, seeds may have reduced seed dormancy so that they germinate rapidly and uniformly. As discussed above, overexpression of HSD reduces dormancy so seeds germinate faster and more completely.

In one aspect of the present invention, the expression of the HSD gene in a plant species is altered by the inhibition of expression of the native HSD gene coding sequence. Accordingly, it is one object of the present invention to alter the expression levels of the protein encoded by the HSD gene normally found in a plant species by introduction of a recombinant HSD gene that alters the expression of the native HSD gene by reduction of the native HSD gene expression and reduction of the levels of the protein encoded by the native HSD gene in said plant species.

It is a further object of the present invention to alter the expression of a native HSD gene in a plant species by introduction of a recombinant version of said HSD gene, said recombinant version altered by the addition of one of more DNA sequences that lead to the increased expression of said gene relative to the expression of the native HSD gene in said plant species, leading to the increased expression levels of the protein encoded by the native HSD gene coding sequence in said plant species.

It is still another object of the present invention to express a non-native HSD coding sequence in a plant species. Said non-native HSD coding sequence can be an altered form of the HSD coding region normally found in said plant species, or a HSD functional homologue from a different plant species. Expression of the non-native HSD protein can be expected to alter the activity of the native HSD protein. An advantage of non-native sequences is that they may be less prone to native regulatory mechanisms and therefore be more effective at producing effects.

Accordingly, it is one object of the present invention to alter expression levels of a hydroxysteroid dehydrogenase protein in a plant by introducing a nucleic acid molecule derived from at least a portion of the nucleic acid sequence as set forth in SEQ ID No. 1, said nucleic acid molecule being arranged for expression in said plant and expression of said nucleic acid molecule leading to altered levels of HSD protein compared to an unmodified control plant.

The nucleic acid molecule may be introduced by transformation as discussed herein.

Accordingly, it is one object of the present invention to alter the activity of the protein encoded by the HSD gene normally found in a plant species by introduction of a recombinant version of a non-native HSD gene, said recombinant version altered by the addition of one of more DNA sequences that lead to expression of said gene in said plant species, leading to altered or enhanced activity of the native HSD protein.

Similarly, it is a further object of the present invention to alter the expression of a native HSD gene in a plant species by introduction of a recombinant non-native HSD gene that alters the activity of the native HSD gene by reduction of the native HSD gene expression and reduction of the expression of the protein encoded by the wt HSD gene in said plant species.

The method further relies on the use of transformation to introduce the gene encoding the enzyme into plant cells. Transformation of the plant cell can be accomplished by a variety of different means. Methods that have general utility include Agrobacterium based systems, using either binary and cointegrate plasmids of both *A. tumifaciens* and *A. rhyzogenies*. (e.g., U.S. Pat. No. 4,940,838, U.S. Pat. No. 5,464,763), the biolistic approach (e.g, U.S. Pat. No. 4,945,050, U.S. Pat. No. 5,015,580, U.S. Pat. No. 5,149,655), microinjection, (e.g., U.S. Pat. No. 4,743,548), direct DNA uptake by protoplasts, (e.g., U.S. Pat. No. 5,231,019, U.S. Pat. No. 5,453,367) or needle-like whiskers (e.g., U.S. Pat. No. 5,302,523). Any method for the introduction of foreign DNA and/or genetic transformation of a plant cell may be used within the context of the present invention.

The method of the present invention relies on the use of well-described techniques to introduce the gene encoding the enzyme into plant cells. Any method for the introduction of foreign DNA and/or genetic transformation of a plant cell may be used within the context of the present invention.

Variations on these methods exist, and the skilled artisan will readily appreciate how these methods may be employed with a plant species of interest as a means to deliver the HSD gene. Thus, it is understood that the method of the present invention is not dependent on any one method for introducing a foreign DNA sequence into a plant cell.

Accordingly, in one further embodiment of the present invention the subject method includes the steps of expressing a HSD gene in a plant species comprising the steps of:
  a) Introducing into a plant cell capable of being transformed a genetic construct comprising a first DNA expression cassette that comprises a DNA sequence that encodes a HSD peptide having at least 50% identity to Seq. ID No. 6, operably linked to a suitable transcriptional regulatory region and,
  b) recovery of a plant which comprises said DNA sequence.

In alternative embodiments, the expression cassette may encode an HSD peptide which is at least 50% identical to the HSD protein described as SEQ ID No. 6; or at least 55% identical, or at least 60% identical, or at least 65% identical, or at least 70% identical, or at least 75% identical, or at least 80% identical, or at least 85% identical or at least 90% identical or at least 95% identical to SEQ ID No. 6.

As will be apparent to one of skill in the art, 'HSD protein' refers to a peptide which retains at least some HSD enzymatic activity.

The suitable transcriptional regulatory region can be the regulatory region normally associated with said HSD coding sequence or a heterologous transcriptional regulatory region capable of expression in a constitutive fashion or in a tissue or cell specific fashion.

In a preferred embodiment of the invention the subject method includes a method for altering the growth of a plant comprising:
  M. Introducing into a plant cell capable of being transformed and regenerated to a whole plant, a genetic construct comprising a DNA sequence derived from Seq. ID. No. 1, operably linked to a suitable transcriptional regulatory region and,
  M. recovery of a plant which contains said recombinant DNA that has altered growth characteristics.

In general, a transgenic plant recovered that expresses the recombinant HSD gene will exhibit altered growth characteristics when compared to the same specific growth characteristics of a non-transformed or mock-transformed or vector-transformed plant of the same species. As will be apparent to one of skill in the art, 'untransformed', 'mock-transformed' and 'vector-transformed' plants will all have unmodified HSD levels and accordingly are used for comparison purposes. It is further noted that these controls need not necessarily be repeated each time. Examples of such altered growth characteristics are described herein and include but are by no means limited to increased seedling vigour, increased mature plant size, increased biomass, increased stress tolerance, increased pathogen resistance and altered seed dormancy characteristics.

In some embodiments, the nucleic acid molecule derived from SEQ ID No. 1 corresponds to a portion or segment of SEQ ID No. 1 or the complement thereof that is sufficient to inhibit expression of the plant's native HSD. As will be appreciated by one of skill in the art, the nucleic acid molecule in these embodiments may be any suitable length, for example, at least 15 nucleotides, at least 20 nucleotides or the like and may correspond to for example the HSD coding region of SEQ ID No. 1 or a portion thereof, the HSD leader sequence of SEQ ID No. 1 or a portion thereof, or the like.

As will be appreciated by one of skill in the art, in these embodiments, HSD levels are lowered by interference with HSD expression, as discussed herein.

In other embodiments, the nucleic acid molecule derived from SEQ ID No. 1 may correspond to a nucleic acid molecule encoding a peptide having at least 50% or at least 55% or at least 60% or at least 65% or at least 70% or at least 75% or at least 80% or at least 85% or at least 90% or at least 95% identical to the amino acid sequence as set forth in SEQ ID No. 6.

As will be appreciated by one of skill in the art, in these embodiments, HSD levels are being increased compared to a control plant of similar type grown under similar conditions, for example, an untransformed plant, a mock transformed plant or a vector transformed plant, as discussed above. As discussed herein, increased HSD levels will accomplish at least one or more of the following: increased seedling vigour, increased mature plant size, increased biomass, increased seed yield, increased stress tolerance, increased pathogen resistance and altered seed dormancy characteristics compared to a control plant as discussed herein.

In a preferred embodiment of the invention the subject method includes a method for altering the salt tolerance of a plant comprising:
  M. Introducing into a plant cell capable of being transformed and regenerated to a whole plant a genetic construct comprising a DNA sequence derived from Seq. ID. No. 1 encoding a HSD gene sequence, operably linked to a suitable transcriptional regulatory region that provides expression of the DNA sequence at least in the roots of said plant, and,
  M. recovery of a plant which contains said recombinant DNA and has increased tolerance to salt stress.

In general, a transgenic plant recovered that expresses the recombinant HSD gene will exhibit the ability to grow at a rate faster than a non-transgenic plant of the same species when both plants are subjected to a salt stress.

In another preferred embodiment of the invention the subject method includes a method for altering seed dormancy of a plant comprising:
  M. Introducing into a plant cell capable of being transformed and regenerated to a whole plant a genetic construct comprising a DNA sequence derived from Seq. ID. No. 1 encoding a HSD gene sequence, operably linked to a suitable transcriptional regulatory region that provides expression of the DNA sequence at least in the seeds of said plant, and,
  M. recovery of a plant which contains said recombinant DNA and produces seeds with altered dormancy characteristics.

In general, a transgenic plant recovered that expresses the recombinant HSD gene will produce seeds that exhibit a change in dormancy that represents at least a two fold alteration of dormancy characteristics, as measured by germination of transgenic seeds relative to non-transgenic seeds of the same species.

In yet another preferred embodiment of the invention the subject method includes a method for producing a plant with enhanced growth characteristics comprising:
  M. Introducing into a plant cell capable of being transformed and regenerated to a whole plant a genetic construct comprising a DNA sequence derived from Seq. ID. No. 1 encoding a HSD gene sequence, operably linked to a suitable transcriptional regulatory region that provides expression in a substantial portion of the plant tissue of a plant, and, M. recovery of a plant which contains said recombinant DNA and exhibits enhanced growth characteristics.

In general, a transgenic plant recovered that expresses the recombinant HSD gene will produce an enhanced growth phenotype that will include, a larger biomass or plant height, increased branching or flowering, or a faster growth rate as measured by the growth of transgenic plants relative to non-transgenic plants of the same species.

The use of gene inhibition technologies such as antisense RNA or co-suppression or double stranded RNA interference is contemplated within the scope of the present invention. In these approaches, the isolated gene sequence is operably linked to a suitable regulatory element.

It is apparent to the skilled artisan that the polynucleotide encoding the sequence can be in the antisense (for inhibition by antisense RNA) or sense (for inhibition by co-suppression) orientation, relative to the transcriptional regulatory region, or a combination of sense and antisense RNA to induce double stranded RNA interference (Chuang and Meyerowitz, PNAS 97: 4985-4990, 2000, Smith et al., Nature 407: 319-320, 2000).

It is obvious to the skilled practitioner that any number of methods for the construction of a heterologous genetic construct encoding the protein or portion thereof encoded by Seq. ID. No. 6 can be used to alter characteristics of a plant wherein said DNA construct has been introduced.

The following examples serve to illustrate the method and in no way limit the utility of the invention

EXAMPLES

Example 1

Isolation of the HSD Gene

The HSD gene was identified in a study of gene expression in germinating and non-germinating *Brassica napus* seeds. Gene expression was monitored by using *Arabidopsis* cDNA microarrays containing about 12,000 probes obtained from the Keck Foundation Biotechnology Resource Laboratory at Yale University School of Medicine and the HSD gene was identified as being expressed in non-germinating seed (Li et al, 2005). To accomplish the isolation of the gene the following procedures were used.

Plant Material and RNA Isolation

Seeds of *B. napus* (DH12075) were imbibed with Polyethylene glycol-8000 (PEG) solution (−1.5 Pa) or ABA analog PBI 429 added from a methanolic stock to give a final concentration of 250 µM. Control seeds for the PEG treatment were soaked in water, and control seeds for the PBI429 treatment were soaked in water containing the same concentration of methanol as in treatments.

Seeds were placed in Petri dishes containing two layers of Whatman filter paper moistened with 4 ml of PEG or PBI429 solution in sterilized water. The Petri dishes were wrapped in foil and incubated in the dark at 23° C. for various periods (6, 12, 24, 36 and 48 hr), then quickly washed and frozen in liquid nitrogen for total RNA isolations.

Fluorescent Labelling of Probe and Purification

Each total RNA sample was converted to cDNA and labelled using the Cyscribe post-Labeling kit (Amersham Bioscience, RPN5660) following the manufacturer's instructions. The CySribe GFX Purification kit (Amersham Bioscience, RPN5660X) was used to purify of the fluorescent dye-labeled cDNA probe by removing free nucleotides and unincorporated CyDye molecules.

Hybridization and Washing

Before prehybridization each spotted slide was denatured in prehybridization buffer (50% formamide, 3.2×SSPE, 0.4% SDS, 2×Denhardt's and 0.177 mg/ml Salmon sperm DNA) at 76° C. for 2 min. The slides were subsequently placed in the hybridization chamber (GeneMachines) for prehybridization at 50° C. for 60 min. After slide prehybridization, the prehybridization buffer was rinsed off by placing the slide in a 50 ml tube for 2 min. first in H2O, then 70% ethanol and then 100% ethanol. The slide was then air dried. Probe/hybridization buffer (62.8% formamide, 0.8% SDS, 4×Denhardts, 5×SSPE) was denatured at 95° C. for 3 min. Then probe solution was placed over the treated slide. A coverslip (Sigma) was applied to the slide and hybridization was performed overnight in a water bath at 42° C. After hybridization, each slide was washed with 200 ml 2×SSC.0.1% SDS once at 42° C. for 4 min., once with 0.2×SSC/0.1% SDS for 4 min. at room temperature, then two times with 0.2×SSC at room time temperature for 2.5 min. each. Slides were placed in 50 ml tube and spun in a swinging bucket rotor centrifuge for 5 min. at 1000 rpm to dry them.

Data Analysis and Quantification

Hybridized slides were scanned sequentially for Cy3- and Cy5-labelled probes with a ScanArray 4000 laser scanner at a resolution of 10 µm. The image analysis and signal quantification were done with QUANTARRAY (GSI Lumonics, Oxnard, Calif.). Clones showing a signal value <800 in both Cy3 and Cy5 channels were eliminated from the analysis. The average of the resulting total Cy5 and Cy3 signals calculated the ratios that were used for normalization. Data storage, preliminary data processing and Lowess normalization was performed with the Bioarray Software Environment (BASE) [49], background-subtracted clone signals were used to calculate Cy5/Cy3 ratios. Further analysis such as data visualization was performed with GeneSpring (Silicon Genetics). Genes/clones with a ratio of treatment/control more than 2.5 or less than 0.4 in at least one time point were selected. The experiments were repeated twice for all time points.

The sequence of this gene was known from the *Arabidopsis* genome sequence and the full-length gene was obtained from a public repository of expressed sequence tags (ESTs).

For identification of HSD-like genes in *Arabidopsis*, the *Arabidopsis* database was searched and as a result a highly homologous cDNA named AtHSD1 (*Arabidopsis* Genome Initiative Locus At5g50600) that encodes a 11-beta-hydroxysteroid dehydrogenase-like gene which belongs to short chain dehydrogenase/reductase (SDR) family protein was found.

Example 2

Characterization of AtHSD1 Gene

Sequence analysis indicated that the AtHSD1 gene is located on chromosome V and consists of six exons and five introns (Sequence ID No. 1). The AtHSD1 cDNA (Sequence ID Nos. 2, 3) encodes 389 amino acid residues (FIG. 1A, Seq ID No. 6) with a calculated molecular mass of 39.0 kD and a isoelectric point of 6.15. The structural analysis of AtHSD1 revealed the presence of an N-terminal transmembrane region (7 to 29 amino acids). The N-terminal half of the AtHSD1 protein is conserved compared with human and mouse HSD proteins (FIG. 1B), whereas the C-terminal half of the protein is not conserved.

Example 3

Construction of Novel HSD Genes

To generate 35S:AtHSD1 sense transgenic lines, Gateway cloning techniques were used to make a DNA construct for gene expression in plant cells. The coding sequence of the AtHSD1 gene was obtained by PCR amplification of cDNA clone U13739 ordered from *Arabidopsis* Biological Resource Center (ABRC), clone U13739 contains full coding sequence of AtHSD1.

The coding region of the AtHSD1 gene was generated by PCR amplification of plasmid Uvi51 (ABRC) containing full coding sequence of this gene, the primers
Seq Id No. 4 (5'-GGGGACAAGTTTGTACAAAAAAG-CAGGCTATGGAGTTGATAAACGACTTTCTC-3')
Seq Id No. 5 (5'-GGGGACCACTTTGTACAA-GAAAGCTGGGTCTAATCCGACTTGATTTCTGGAG T-3')
(attB sites for recombination cloning are shown in bold, and the sequence corresponding to AtHSD1 is underlined) were used for PCR. For generating AtHSD1 overexpression lines, the PCR product was introduced into the binary vector pK7WG2 (Mansour et al. 2002) using Gateway technology. The insert in the construct was sequenced to confirm the orientation and sequence.

Example 4

Transformation of *Arabidopsis*

The construct was transformed into *A. tumefaciens* strain GV3101, and transformed into *Arabidopsis* (var. Columbia) by the floral dip method (Clough and Bent, 1998).

Example 5

Transformation of *Brassica*

*Brassica napus* was also transformed with this construct using the Cotyledonary Petiole Based System (Moloney et al. 1989, U.S. Pat. No. 5,750,087).

Example 6

Increased Yield and Growth of Transgenic *Arabidopsis* (AOHSD) and *Brassica* (BOHSD) Relative to Wild-type Plants In *Arabidopsis*, to determine seed yield, plants were dried for one week at room temperature. Seeds were harvested from individual plants and weighed, mean values of n=12. The number of branches and height at maturity were measured at 60 days after germination (n>9). Phenotypes of individual *Brassica napus* plants were visualized at one month after germination and inflorescences of 6-week-old *Brassica* wild type and transgenic plants were compared.

Figure 3:
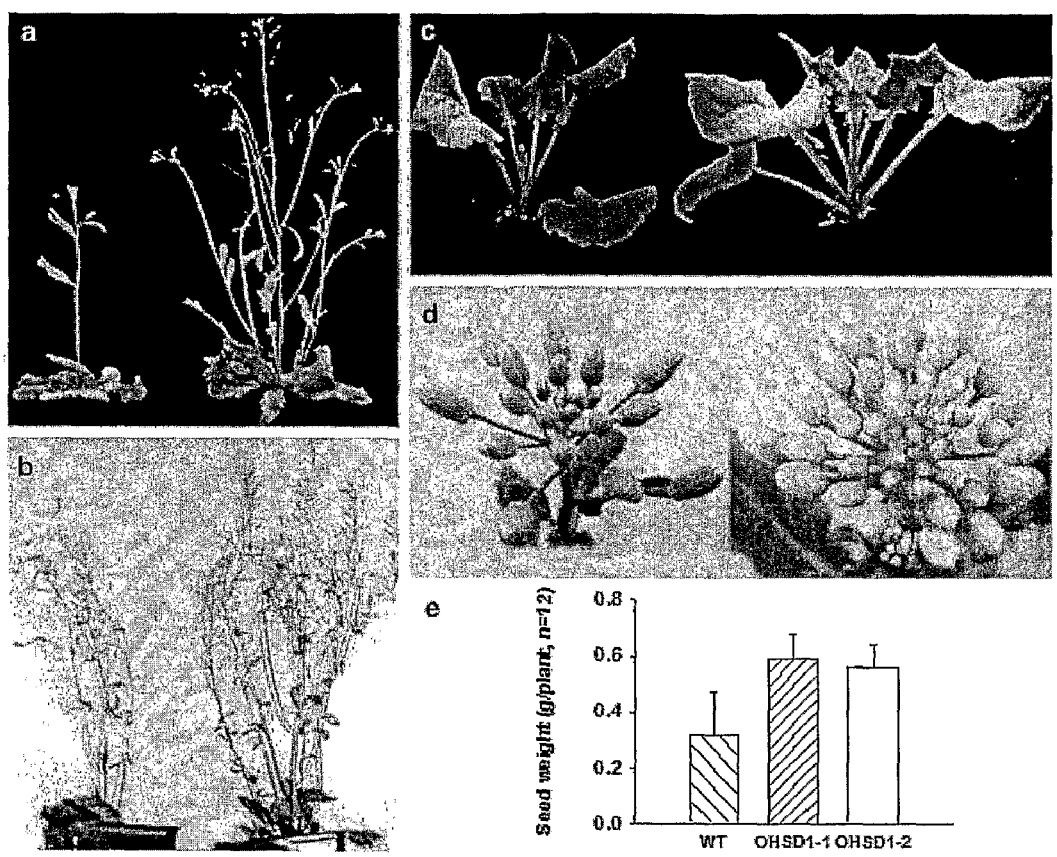
FIG. 3: Shows a comparison of the phenotypes of transgenic *Arabidopsis thaliana* (AOHSD) and transgenic *Brassica napus* (BOHSD) plants at later stages of developmental. (a) Appearance of a month-old AOHSD plant (right) and wild type plant (left). (b) Appearance of two-months old wild type (left) and AOHSD16 (right) plants. (c) Appearance of a month-old control (left) and BOHSD2 (right) plants. (d) Comparison of 6-week-old wild type (left) and BOHSD2 (right) flower clusters. (e) Seed weights per plant of wild type and AOHSD16, n=12.

In both *Brassica napus* and *Arabidopsis thaliana*, transformed plants were larger and grew faster than control plants as shown in FIGS. 2 and 3.

Example 7

Reduced Seed Dormancy and Insensitivity to ABA in *Brassica* and *Arabidopsis*

Plants were grown under a 16-h photoperiod at 22° C. Seeds used for comparison were as close as possible in age. Before plating, seeds were surface sterilized by incubation in 10% (v/v) bleach, 0.01% (v/v) SDS for 10 min, followed by four washes with sterile water, then seeds were germinated on 0.8% (g/v) agar containing 1× Murashige and Skoog (MS) basal salt mixture under different conditions. For ABA insensitivity experiments, the medium contained varying concentration of ABA (from 0.1 to 100 µM).

Figure 4:
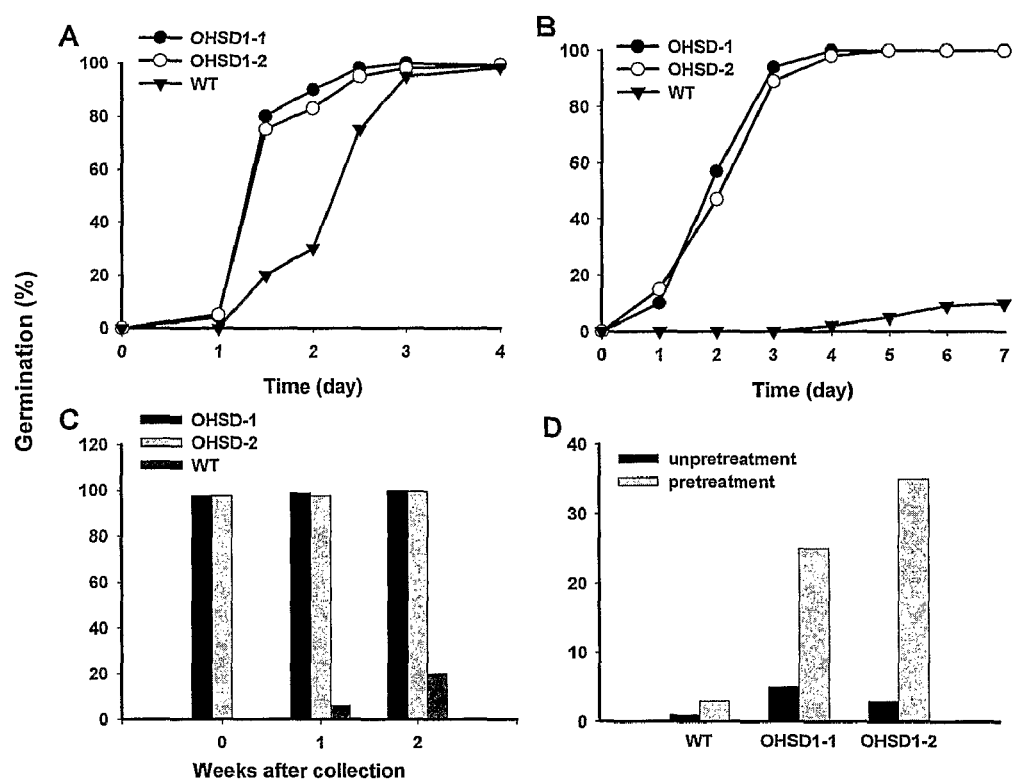
FIG. 4: Shows the reduction in the dormancy of transgenic *Arabidopsis* lines (AOHSD1-1 and AOHSD1-2). Percent germination was determined from 120 seeds of each line. A. Time course of germination of overexpression line and wild type seeds stored for 4 weeks at room temperature but without stratification at 4° C. B. Time course of germination of overexpression line and wild type seeds that were freshly harvested. C. Germination of overexpression line and wild type seeds after storage at room temperature for 0, 1, 2 weeks. Germination was scored after 7 days of incubation. D. Germination of freshly harvested overexpression line and wild type seeds in darkness with or without one day pretreatment at 4° C. Germination was scored after 7 days of incubation.

Results show that transgenic lines have almost no primary dormancy relative to wild-type seeds (FIGS. 4A and B) and germinate much faster. In wild-type seed, primary dormancy is lost during storage, whereas storage has almost no effect on transgenic seed (FIG. 4C). However, transgenic seeds incubated in the dark exhibit little difference in germination from the wild-type unless they are briefly cold-treated (stratified) at 4° C. This cold treatment is insufficient to significantly increase WT germination, but produces a large increase in germination of transgenic seed (FIG. 4D). Therefore, transgenic seed exhibits dormancy in the dark but are hypersensitive to dormancy-breaking cold treatment. It is also clear that light is required to fully express the germination-promoting effects of the HSD gene.

Figure 5:
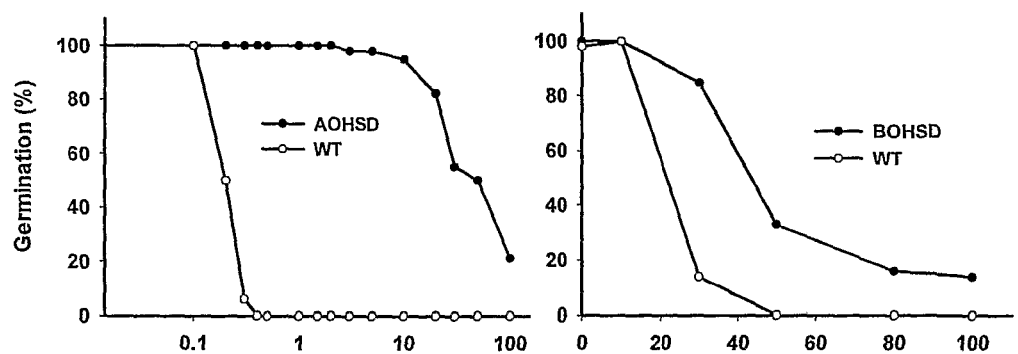
FIG. 5: Shows a comparison germination of transgenic *Arabidopsis* and wild type *Arabidopsis* seed at varying concentration of ABA. Also shown is a comparison of transgenic *Brassica* and wild type *Brassica* seed at varying concentration of ABA. Compares percent germination of Col wild-type (o) to *Arabidopsis* (AODSH) transgenic seeds (•) (A) and of *Brassica napus* wild type to *Brassica* (BODSH) transgenic seeds (B). Percent germination was determined for greater than 120 seeds for *Arabidopsis* and more than 30 seeds for *Brassica napus*.

Transgenic seeds of both *Arabidopsis* and *Brassica napus* were insensitive to exogenously applied ABA relative to WT, although the effect was more pronounced in *Arabidopsis* (FIG. 5). WT *Brassica napus* seeds are approximately two orders of magnitude less sensitive to ABA that WT *Arabidopsis* seeds.

Example 8

Enhanced *Arabidopsis* Tolerance to Salt Stress

For mature plant salt stress tolerance experiments, two-week-old *Arabidopsis* plants grown under a 16-h photoperiod at 22° C. were flooded once a week during the subsequent 4 weeks with 100, 200, 300, 400 mM NaCl.

For seedling stage salt stress tolerance experiments, seeds were surface sterilized by incubation in 10% (v/v) bleach. 0.01% (v/v) SDS for 10 min, followed by four washes with sterile water, then seeds were germinated and grown two weeks on MS medium containing 100 mM NaCl.

Figures 1, 6:
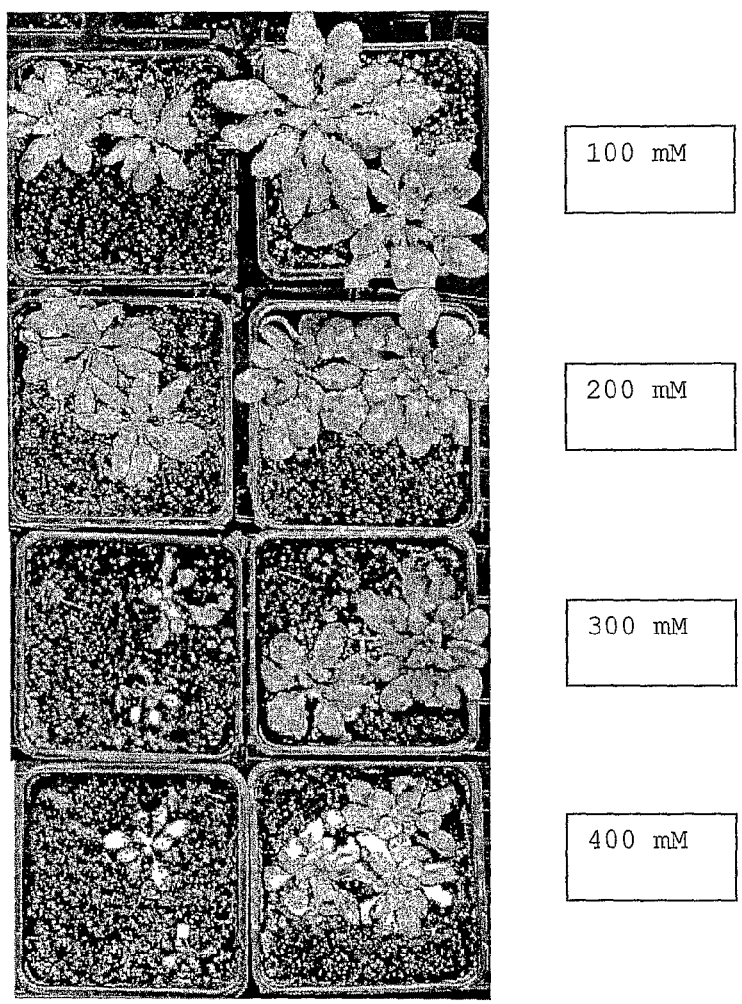
FIG. 6: Shows the comparative effect on survival of NaCl stress on transgenic and wild type *Arabidopsis* seed flooded weekly with 100, 200, 300, and 400 mM solutions of NaCl. Also shown is a comparison of transgenic *Brassica* and wild type *Brassica* seed at varying concentration of NaCl. (A) Two-week-old plants were flooded once a week during the subsequent 4 weeks with 100, 200, 300, and 400 mM NaCl.
Figures 2, 6:

Results show that both mature transgenic plants and transgenic seedlings of *Arabidopsis* are more resistant to salt stress than corresponding WT material. Transgenic plants grow and stay green at higher salt concentrations than WT plants (FIGS. 6A and 6B).

Example 9

Enhanced *Brassica napus* Tolerance to Heat Treatments

Seedlings (1 week after germination) were subjected to a brief (2 h) exposure to a temperature of 45° C. (heat shock). They were then returned to normal growth conditions for 7 days. The untransformed (control) planta are cultivar DH12075; two representative transgenic lines (LF19 and LF22) are shown that overexpress the HSD gene under the control of the cauliflower mosaic virus 35S promoter.

| Lines | Healthy % | Recovering % | Dead % |
|---|---|---|---|
| Control | 20.0 | 46.2 | 33.7 |
| LF19 | 64.8 | 14.3 | 22.5 |
| LF22 | 61.7 | 28.8 | 9.5 |

The transgenic lines are substantially more viable after heat shock treatment than the control plants.

Example 10

*Brassica napus* Plants are Taller, Flower Earlier and Contain More Inflorescences The height of plants and the number of inflorescences (flowering shoots) per plant were counted after 52 days of growth. Numbers were calculated from 10 plants of each type. The lines LF19 and LF22 are two representative transgenic lines that overexpress the HSD gene.

| Lines | Plant height (inches) | Inflorescences per plant | Number of plants flowering (out of 10) |
|---|---|---|---|
| control | 11.8 | 1.2 | 2 |
| LF19 | 12.3 | 3.4 | 4 |
| LF22 | 17.5 | 4.8 | 8 |

Example 11

*Brassica napus* Plants Produce More Seed Weight than Parental Plants

| Lines | Average weight of seed per plant (g) |
|---|---|
| control (10 plants) | 2.79 (100%) |
| Mixed transgenic lines (16 plants) | 3.18 (114%) |

Example 12

*Brassica napus* Plants are More Resistant to Low Temperature Stress

Seedlings grown for 2 weeks were subjected to a low temperature treatment consisting of a 4 day acclimation period at 40 C for 4 days then slow cooling to −80 C for 6 h, followed by a slow recovery period to normal growth conditions. The number of plants surviving this treatment was counted 2 d and 14 d afterwards. A representative transgenic line (LF22) was compared to untransformed (control) plants (DH12075).

| Lines | % alive after 2 days | % alive after 2 weeks |
|---|---|---|
| control | 48.3 | 24 |
| LF22 | 73.3 | 67 |

Example 13

*Brassica napus* Plants Grow Better on Low Nutrients

Plants were grown in Sunshine soil mixture #2 with no supplemental nutrients (fertilizer) for one month. The length of the 4th leaf was measured.

| Lines | Average length of 4th leaf (cm) | Average number of leaves |
|---|---|---|
| control | 4.7 | 4.0 |
| LF19 | 6.9 | 4.6 |
| LF22 | 6.9 | 4.6 |

Transgenic plants were larger than untransformed plants as quantified by the size of the 4th leaf and the average number of leaves per plant.

Example 14

Increased Total Oil Content in Seeds of *Brassica napus*

Dry seeds from selected lines were analyzed for total oil content by Gas chromatography. Twelve seeds from each line were analyzed.

| Lines | % oil |
|---|---|
| control | 30.2 |
| LF19 | 36.9 |
| LF22 | 33.7 |

While the preferred embodiments of the invention have been described above, it will be recognized and understood that various modifications may be made therein, and the appended claims are intended to cover all such modifications which may fall within the spirit and scope of the invention.

REFERENCES

U.S. Patent Documents

| | | |
|---|---|---|
| 4,346,226 | March 1982 | Thompson et al |
| 4,743,548 | May 1988 | Crossway et al |
| 4,940,838 | July 1990 | Schilperoort et al |
| 4,945,050 | July 1990 | Sanford et al |
| 5,015,580 | May 1991 | Christou et al |
| 5,149,655 | September 1992 | McCabe et al |
| 5,231,019 | July 1993 | Paszkowski et al |
| 5,302,523 | April 1994 | Coffee et al |
| 5,453,367 | September 1995 | Paszkowski et al |
| 5,464,763 | November 1995 | Schilperoort et al |
| 5,750,871 | May 1998 | Moloney et al |
| 5,952,545 | September 1999 | Koncz et al |
| 6,245,969 | June 2001 | Chory & Li |
| 6,534,313 | March 2003 | Neff & Chory |
| 6,605,469 | August 2003 | Kang & Park |
| 6,765,085 | July 2004 | Chory & Li |
| 6,768,043 | July 2004 | Chory & Wang |
| 6,921,848 | July 2005 | Chory & Wang |

OTHER REFERENCES

Li, F., et al., (2005) Transcriptional profiling of imbibed *Brassica napus* seed. Genomics. In Press.

Clough, S. J. and Bent, A. F. (1998) Floral dip: a simplified method for Agrobacterium-mediated transformation of *Arabidopsis thaliana*. Plant J. 16, 735-743.

M. M. Moloney, et al. (1989) Plant Cell Reports 8: 238-242.

Bishop, G. J., et al., (1999). The tomato DWARF enzyme catalyzes C-6 oxidation in brassinosteroid biosynthesis. Proc. Natl. Acad. Sci. USA 96, 1761-1766.

Choe, S., at al., (1998). The DWF4 gene of *Arabidopsis* encodes a cytochrome P450 that mediates a multiple 22.alpha.-hydroylation steps in brassinosteroid biosynthesis. Plant Cell 10, 231-243.

Choe, S., et al., (1999a). The *Arabidopsis* dwarf1 mutant is defective in the conversion of 24-methylenecholesterol to campesterol in brassinosteroid biosynthesis. Plant Physiol. 119, 897-907.

Choe, S., et al., (1999b). The *Arabidopsis* dwf7/ste1 is defective in the delta7 sterol C-5 desaturation step leading to brassinosteroid biosynthesis. Plant Cell 11, 207-221.

Clouse, S. D., and Sasse, J. M. (1998). Brassinosteroids: Essential regulators of plant growth and development. Annu. Rev. Plant Physiol. Plant Mol. Biol. 49, 427-451.

Fujioka, S., at al., (2000). Biosynthesis of brassinosteroids in cultured cells of *Catharanthus roseus*. Phytochem 53; 549-553.

Grove, et al., Nature, 281:216 1979.

Li, J., and Chory, J. (1997). A putative leucine-rich repeat receptor kinase involved in brassinosteroid signal transduction. Cell 90, 929-938.

Li, J, Nagpal et al., (1996). A role for brassinosteroids in light-dependent development of *Arabidopsis*. Science 272, 398-401.

Mandava, et al., Ann. Rev. Plant Physiol. Plant Mol. Biol., 39:23, 1988

Noguchi, et al., (2000), Biosynthetic pathways of brassinolide in *Arabidopsis*, Plant Phsiol. 124: 201-209

Nomura, T., Kitasaka et al., (1999). Brassinosteroid/sterol synthesis and plant growth as affected by Ika and Ikb mutations of pea. Plant Physiol. 119, 1517-1526.

Wang et al., (2001) BRI1 is a critical component of a plasma-membrane receptor for plant steroids. Nature, 410: 380-383.

The invention claimed is:

1. A method for altering growth characteristics of a plant comprising: introducing into a plant cell capable of being transformed and regenerated to a whole plant, a genetic construct comprising a DNA sequence encoding the peptide as set forth in SEQ ID No. 6, the DNA sequence operably linked to a suitable transcriptional regulatory region and, recovering a plant which contains said recombinant DNA sequence, and which has at least one of increased seed yield, increased seed mass, increased seedling vigour, increased plant vegetative growth, increased mature plant size, increased biomass, improved growth in nutrient-poor soil, shorter time to maturity, increased tolerance to abiotic stress, increased oil content, altered hormone sensitivity and altered seed dormancy, compared to a control plant of similar type grown under similar conditions.

2. The method according to claim 1 wherein the altered growth characteristics comprise increased tolerance to abiotic stress, and the increased tolerance to abiotic stress comprises at least one of increased salt tolerance, increased temperature tolerance, decreased sensitivity to ABA and decreased sensitivity to brassinosteroids.

3. The method according to claim 2, wherein the DNA sequence is as set forth in SEQ ID NO: 1.

4. The method according to claim 2, wherein the DNA sequence inhibits expression of the plant's native hydroxysteroid dehydrogenase.

5. The method according to claim 1, wherein the DNA sequence is as set forth in SEQ ID NO: 1.

6. The method according to claim 1, wherein the DNA sequence inhibits expression of the plant's native hydroxysteroid dehydrogenase.

* * * * *